United States Patent [19]
Ansorge et al.

[11] Patent Number: 5,976,802
[45] Date of Patent: Nov. 2, 1999

[54] SIMULTANEOUS SEQUENCING OF NUCLEIC ACIDS

[75] Inventors: Wilhelm Ansorge, Gaiberg; Hartmut Voss, Leimen; Josef Stegemann, Heidelberg; Stefan Wiemann, Eppelheim, all of Germany

[73] Assignee: Europäsches Laboratorium für Molekularbiologie (EMBL)

[21] Appl. No.: 08/913,990

[22] PCT Filed: Apr. 26, 1996

[86] PCT No.: PCT/EP96/01762

§ 371 Date: Sep. 29, 1997

§ 102(e) Date: Sep. 29, 1997

[87] PCT Pub. No.: WO96/34114

PCT Pub. Date: Oct. 31, 1996

[30] Foreign Application Priority Data

Apr. 27, 1995 [DE] Germany ............. 195 15 552

[51] Int. Cl.⁶ ............. C12Q 1/68; G01N 33/53; C12P 19/34; C07H 21/00
[52] U.S. Cl. ............. 435/6; 435/7.1; 435/91.1; 435/91.2; 536/25.32
[58] Field of Search ............. 435/6, 7.1, 91.2, 435/91.1; 536/25.32

[56] References Cited

U.S. PATENT DOCUMENTS

| | | | |
|---|---|---|---|
| 5,173,411 | 12/1992 | Tabor et al. | 435/91 |
| 5,266,466 | 11/1993 | Tabor et al. | 435/91.5 |
| 5,302,509 | 4/1994 | Cheeseman | 435/6 |

FOREIGN PATENT DOCUMENTS

| | | |
|---|---|---|
| 41 41 178 A1 | 6/1993 | Germany . |
| WO 93/20232 | 10/1993 | United Kingdom . |

OTHER PUBLICATIONS

Wiemann S. et al. Simultaneous DNA sequence on both strands with two dyes. Genome Mapping and Sequencing p. 271, 1993.

Kambara, H. et al. Real time automated simultaneous double stranded DNA sequencing using wto color fluorophore labeling. Bio/Technology vol. 9 pp. 648–651, 1991.

Voss, H. et al. New procedure for automated DNA sequencing with Multiple Internal Labeling by fluroescent dUTP. Meth. Mol. Cell. Bio. vol. 3. pp. 30–34, 1992.

Voss, H. et al. Automated Low Redundancy Large Scale DNA Sequencing by Primer Walking. BioTechniques. vol. 15, No. 4, pp. 714–721, 1993.

Lee, L.G. et al. DNA sequencing with dye–labeled terminators and T7 DNA polymerase: effect of dyes and dNTPs on incorporation of dye–terminators and probability analysis of termination fragments. Nucleic Acid Research. vol. 20, No. 10, pp. 2471–2483, 1992.

(List continued on next page.)

*Primary Examiner*—Kenneth R. Horlick
*Assistant Examiner*—Jeffrey Siew
*Attorney, Agent, or Firm*—Nikaido Marmelstein Murray & Oram, LLP.

[57] ABSTRACT

The invention concerns a method for the sequence-specific labelling of nucleic acids comprising the generation of labelled nucleic acid fragments by an enzymatic labelling reaction in which a labelled deoxyribonucleoside triphosphate is attached to a nucleic acid primer molecule and the nucleic acid sequence is determined by means of the label, wherein the labelling reaction is carried out in a single reaction vessel with the simultaneous presence of one or several nucleic acid primer molecules and at least two labelled deoxyribonucleoside triphosphates which each contain different labelling groups and different bases and under conditions in which only one single type of labelled deoxyribonucleoside triphosphate can be attached to a nucleic acid primer molecule.

23 Claims, 5 Drawing Sheets

OTHER PUBLICATIONS

–Smith, L.M. et al Fluroescence detection in automated DNA sequence analysis Nature vol. 321, No. 6071 pp., 1986.

Analytical Biochemistry, vol. 234, Feb. 10, 1996, pp. 166–174, "Doublex Fluorescent DNA Sequencing: Two Independent Sequences Obtained Simultaneously in One Reaction with Internal . . . ".

Analytical Biochemistry, vol. 224, Jan. 1, 1995, pp. 117–121, "Simutaneous On–line DNA sequencing of both strands with two fluorescent dyes".

International Application No. WO 93/03180 published Feb. 18, 1993.

International Application No. WO 93/06243 published Apr. 1, 1993.

International Application No. WO 89/03432 published Apr. 20, 1989.

International Application No. WO 94/01447 published Jan. 20, 1994.

International Application No. WO 92/15712 published Sep. 17, 1992.

SIMULTANEOUS SEQUENCING OF NUCLEIC ACIDS

The present invention concerns a method for the sequence-specific labelling and simultaneous sequencing of nucleic acids comprising the production of labelled nucleic acid fragments by an enzymatic labelling reaction in which a labelled deoxyribonucleoside triphosphate is attached to a nucleic acid primer molecule and the nucleic sequence is determined by means of the label.

In DNA sequencing by the enzymatic chain termination method according to Sanger one starts with a nucleic acid template from which many labelled nucleic acid fragments of various length are produced by an enzymatic extension and termination reaction in which a synthetic oligonucleotide primer is extended and terminated with the aid of polymerase and a mixture of deoxyribonucleoside triphosphates (dNTP) and chain termination molecules, in particular dideoxyribonucleoside triphosphates (ddNTP).

In this method a mixture of the deoxyribonucleoside triphosphates (dNTPs) and one dideoxyribonucleoside triphosphate (ddNTP) is used in each of four reaction mixtures. In this manner a statistical incorporation of the chain termination molecules into the growing nucleic acid chains is achieved and after incorporation of a chain termination molecule the DNA chain cannot be extended further due to the absence of a free 3'-OH group. Hence numerous DNA fragments of various length are formed which, from a statistical point of view, contain a chain termination molecule at each potential incorporation site and end at this position. These four reaction mixtures which each contain fragments ending at a base due to the incorporation of chain termination molecules are separated according to their length for example by polyacrylamide gel electrophoresis and usually in four different lanes and the sequence is determined by means of the labelling of these nucleic acid fragments.

Nowadays DNA sequencing is carried out with automated systems in which usually a non-radioactive label, in particular a fluorescent label, is used (L. M. Smith et al, Nature 321 (1986), 674–679; W. Ansorge et al, J. Biochem. Biophys. Meth. 13 (1986), 315–323). In these automated systems the nucleotide sequence is read directly during the separation of the labelled fragments and entered directly into a computer.

In the automated methods for sequencing nucleic acids non-radioactive labelling groups can either be introduced by means of labelled primer molecules, labelled chain termination molecules or as an internal label via labelled dNTP. In all these known labelling methods the sequencing reactions are in each case carried out individually in a reaction vessel so that always only one single sequence is obtained with a sequencing reaction.

A method for sequencing nucleic acids is described in the International Patent Application WO 93/03180 in which nucleic acid fragments are determined after incorporation of at least one non-radioactively labelled dNTP as an internal label wherein the internal label is incorporated into the nucleic acid fragments in the absence of chain termination molecules.

The simultaneous determination of two nucleic acid sequences using two differently labelled primer molecules in a single reaction vessel was described by Wiemann et al (Anal. Biochem. 224 (1995) 117–121). However, a disadvantage of this method is that dyelabelled oligonucleotide primers have to be used which are expensive or/and complicated to produce. This is a particular disadvantage when sequencing longer gene sections using the walking primer strategy in which different primers have to be used for each sequencing reaction. Moreover the use of labelled primers sometimes impedes the hybridization of the primer with the nucleic acid template which can lead to inaccurate sequencing results.

In order to avoid this disadvantage one could carry out two sequencing reactions each with an unlabelled primer and one of two differently labelled dNTP in two separate reaction vessels, mix both products, apply them simultaneously to a gel and determine the sequences. However, a disadvantage of this method is that it is laborious and complicated to carry out two sequencing reactions in separate reaction vessels.

Thus the object of the present invention was to provide a method for the sequence-specific labelling and sequencing of nucleic acids in which the disadvantages of the state of the art are at least partially eliminated. In particular the method according to the invention should enable two or more sequencing reactions to be carried out simultaneously in a single reaction vessel using at least two differently labelled dNTP and at least two preferably unlabelled primer molecules.

The object of the invention is achieved by a method for the sequence-specific labelling of nucleic acids comprising the production of labelled nucleic acid fragments by an enzymatic labelling reaction in which a labelled deoxyribonucleoside triphosphate is attached to a nucleic acid primer molecule and the nucleic acid sequence is determined by means of the label, the method being characterized in that the labelling reaction takes place in a single reaction vessel with the simultaneous presence of one or several nucleic acid primer molecules and at least two labelled deoxyribonucleoside triphosphates which each contain different labelling groups and different bases and under conditions in which only one single type of labelled deoxyribonucleoside triphosphate can be attached in each case to a nucleic acid primer molecule.

The nucleic acid primer molecule is a nucleic acid, preferably a DNA, which is sufficiently complementary to a nucleic acid present in the reaction mixture to be able to hybridize with it under the respective reaction conditions. The length of the primer molecule is preferably 10–100, particularly preferably 12–50 and most preferably 12–30 nucleotides.

The enzymatic labelling reaction is carried out in the method according to the invention such that only one single type of labelled dNTP and preferably only one single type of labelled dNTP and preferably only one single labelled dNTP is attached in each case to a nucleic acid primer molecule. The labelled dNTP is preferably attached directly to the 3' end of the primer (position +1). In this case the base of the labelled dNTP is complementary to that base which is located on the nucleic acid hybridizing with the primer molecule directly on the 5' side of the complementary region to the primer. If it can be ensured that only one single type of label is incorporated behind each primer, the label can also be incorporated at a greater distance from the 3' end of the primer (positions +2, +3, +4 etc.). In addition to the at least two differently labelled dNTPs, unlabelled dNTPs may also be present in the labelling reaction.

However, the sequence of one or several primer molecules can also be selected such that, when using a polymerase with 3' exonuclease activity, the labelled dNTPs are inserted as a terminal base of the primer or primers in an exchange reaction when the 3' terminal base of the primer is the same as the base used for the labelled dNTP.

When carrying out the enzymatic labelling reaction the conditions are chosen such that statistically only one single type of labelled deoxyribonucleoside triphosphate can be attached to the primer. In order to achieve this reaction specificity the reaction conditions (such as the concentration of the polymerase enzyme or/and dNTP, temperature, concentration of other components etc.) are preferably selected accordingly. In addition the specificity of the reaction can be increased by selection of the primer molecules as explained in the following.

The method according to the invention enables for example the simultaneous sequencing of DNA fragments with two or several primer molecules, preferably unlabelled primer molecules, and several labelled dNTPs in one reaction vessel. Several labelling reactions can be carried simultaneously on different strands of the nucleic acid to be sequenced or at various sites on the same nucleic acid strand. The specificity of the method according to the invention is surprisingly so high that statistically a single type of label, in particular only one single labelled dNTP is attached to a particular primer molecule even if several other differently labelled dNTP, primer molecules and nucleic acid template molecules are present in the same reaction vessel.

The combination of one or several DNA templates and of two or several primer molecules and labelled dNTPs in a single sequencing reaction enables the costs for carrying out the sequencing reactions to be reduced by 50–75%. There is a reduction in the costs for the chemicals as well as for the amount of work required. This is of particular importance for large scale sequencing projects such as the human genome sequencing project or other genome projects.

There is a wide range of application forms for the method according to the invention e.g. sequencing, mapping and selective labelling of DNA fragments in medical diagnostics, molecular biology, biochemistry and chemistry. The most important form of application is automated DNA sequencing with fluorescent marker groups.

Specific forms of application are the so-called minisequencing in which the nucleic acid sequence is only determined within a limited region of up to three bases after the primer based on a sequence-specific incorporation of the labelled dNTP. A further possible application is to detect point mutations in genes, in particular in human genes. In this case the primer molecule is selected such that it lies immediately in front of a hot spot of the mutation. Only one primer is used together with two or several differently labelled dNTP and the labelling reaction is carried out. Only a single labelled dNTP is incorporated which is complementary to the corresponding base on the nucleic acid template. Subsequently the extended primer molecule can be analysed and the labelling group can be identified by its spectral characteristics. In this manner it is possible to draw conclusions about the sequence of the respective gene.

When used to determine the sequence of nucleic acids, the method according to the invention is preferably carried out by a) binding at least one nucleic acid primer molecule to the nucleic acid to be sequenced, b) adding a polymerase and at least two labelled deoxyribonucleoside triphosphates which each contain different labelling groups and different bases, c) incubating the reaction mixture in a single reaction vessel under such conditions that in each case only a single type of labelled deoxyribonucleoside triphosphate is attached to a primer molecule and d) determining one or several nucleic acid sequences by means of the sequence-specific incorporation of the labelled deoxyribonucleoside triphosphates.

In the method according to the invention at least two labelled deoxyribonucleoside triphosphates are used in each case in a reaction mixture which each contain different labelling groups and different bases i.e. a maximum of four deoxyribonucleoside triphosphates (corresponding to the bases A, T, C and G) can be used each of which carries a different labelling group. The labelling groups can be radioactive or non-radioactive labels and it should be possible to detect them concurrently. Non-radioactive labelling groups are preferred in particular fluorescent labelling groups e.g. fluorescent dyes such as rhodamine, derivatives of rhodamine such as methylrhodamine, Texas red,. phycoerythrin, fluorescein and derivatives thereof, CY3, CY5, CY2, CY7, coumarin, infrared 40, MR 200, bodipy dyes (molecular probes), $1,N^6$-etheno modification groups for dNTPs (molecular probes), IRD 40 etc. Other suitable non-radioactive labelling groups are for example metals, magnetic labelling groups which can be detected by nuclear resonance or by a supra-conducting quantum interferometric detector (SQID) or phosphorescent dyes. Suitable excitation or/and detection systems can be used to determine the respective labels.

Examples of commercially available fluorescent labelled dNTP are for example fluorescein-dUTP, fluorescein-dATP (Boehringer Mannheim, Pharmacia); Texas red-dCTP and dGTP (NEN-Dupont), CY5-dATP and dCTP as well as CY3-dATP (Pharmacia).

It is expedient to use fluorescent labelling groups which can be detected concurrently. Thus one can for example use two or several different laser systems to excite the fluorescent groups which are coupled to appropriate detection systems. Thus for example fluorescein labelling groups can be detected in automated DNA sequencing systems with an argon laser (emission wavelength=488 nm) and appropriate detectors. A helium-neon laser (emission wavelength=594 nm) can for example be used as a second laser with appropriate detectors to detect nucleic acids labelled with Texas red. Interferences between both laser systems can be substantially suppressed by band pass filters. The data are recorded by two detector instruments, one for each laser. On the other hand it is also possible to use combinations of fluorescent dyes which can be excited by a single laser system and separately determined by different detection systems in each case.

The concentration of the labelled dNTPs during the labelling reaction is preferably so low that at a given polymerase concentration essentially only a single labelled dNTP can be coupled to a primer molecule. The labelled dNTPs are therefore preferably used at a concentration of 0.05–5 µmol/liter, particularly preferably at a concentration of 0.1–2.5 µmol/liter. At such a dNTP concentration the polymerase present in the reaction mixture can statistically only attach a single dNTP molecule to a primer. The polymerase concentration is preferably 1–20 U, particularly preferably 5–15 U per reaction mixture. It may be critical to adhere to the above-mentioned concentration ranges especially when using several primer molecules simultaneously since when the dNTP or/and enzyme concentration is too high several differently labelled dNTP may be attached to a single primer.

Furthermore the specificity of the incorporation of labelled dNTPs can be influenced by the selection of the labelling molecule (e.g. fluorescein, Texas red etc.), by the selection of the dNTP (dUTP, dTTP, DATP, dCTP, dGTP etc.) or/and by the type of linkage between the dNTP and the labelling molecule (e.g. length of the spacer arm).

In order to enzymatically attach a dNTP to the primer molecule, a polymerase, preferably the Klenow fragment of the *E. coli* DNA polymerase I, unmodified T7 DNA polymerase, modified T7 DNA polymerase (Sequenase), T4 DNA polymerase, Taq DNA polymerase, Bst DNA polymerase or reverse transcriptase is used in the method according to the invention. Of these enzymes polymerases without a 3' exonuclease activity are preferred e.g. modified T7 polymerase.

In particular embodiments of the invention polymerases with a 3' exonuclease activity e.g. unmodified T7 polymerase may, however, be preferred for example if the labelled deoxyribonucleoside triphosphate is inserted as the last base of the primer molecule (position −1) by sequential exonuclease and polymerase activities.

An advantage of the method according to the invention is its simplicity since no labelled primer molecules are required. This is particularly significant for large scale sequencing projects such as the sequencing of the human genome or other genome projects. On the other hand labelled primers can of course also be used if desired in order to optionally obtain additional information about the nucleic acid sequence. Furthermore the sequencing reactions can be carried out with a combination of unlabelled and labelled (fluorescent dyes or of another type e.g. digoxigenin, biotin, metals etc.) primers in which case the primer is preferably selected such that the internal label is in each case only attached to the unlabelled primer. The labelled primers preferably carry labelling groups that are different to those of the labelled dNTPs.

When nucleic acids are sequenced simultaneously using two or more primer molecules, the selection of the primer molecules is important. Thus the primers must be followed by different nucleotides which are incorporated as the next base when the primer is extended by the polymerase. In this manner only one type of labelling group is attached in each case to one type of primer molecule in the labelling reaction. The incorporation of other labelling groups can be excluded by selecting the reaction conditions in the labelling reaction.

A preferred embodiment of the present invention concerns a method in which at least two primer molecules are used which bind to different regions of the nucleic acid to be sequenced wherein the primer molecules are selected such that in each case the next base to be attached at their 3' end is different and wherein a labelled deoxyribonucleoside triphosphate with a corresponding base is used for each primer molecule such that only one single different labelled deoxyribonucleoside triphosphate is attached to each primer molecule. In the present application the base at the 3' end of a primer molecule is referred to in each case as "position −1" for the sake of clarity. The next base to be attached by the polymerase to the 3' end of the primer molecule is referred to as "position +1" and the base after that is referred to as "position +2".

Further criteria should also be observed preferably when constructing the primer molecules to increase the specificity of the labelling reaction. Thus in one reaction mixture one preferably uses only those primer molecules in which the base which is to be attached next at the 3' end of the primer (position +1) is not the same as the base that is to be attached next but one (position +2) at the 3' end of another primer. This reduces the probability that a primer molecule is labelled with two different labelling groups.

Furthermore it is preferred that primer molecules are used in which the base at the 3' end of a primer molecule (position −1) is not the same as the next base (position +1) to be attached to the 3' end of another primer molecule. In this manner it is possible to avoid potential double labelling due to a 3' exonuclease activity of the polymerase enzyme used.

If a polymerase without 3' exonuclease activity is used e.g. modified T7 polymerase it is not absolutely necessary to follow this selection criterium.

If two or several primer molecules are used it is possible to simultaneously determine two or several nucleic acid sequences by the method according to the invention.

The sequencing reaction of the method according to the invention is usually carried out in two steps. Firstly a single type of labelled dNTP is attached to the 3' end of the primer in a labelling reaction. It is particularly preferred that only a single labelled dNTP is attached to a primer in each case. The primer is preferably selected such that the labelled dNTP can be attached to its 3' end (position +1). Furthermore it is preferred that in the labelling reaction only labelled dNTP are present since, if there is an undesired binding of the primer to secondary binding sites on the template, this reduces the probability of incorporating labelled dNTPs. Finally the use of a DNA polymerase without 3' exonuclease activity e.g. Sequenase® is also preferred especially when a primer ends with a nucleotide which is present as a labelled dNTP in the labelling reaction mixture.

As a next step an extension reaction takes place until a chain termination molecule is incorporated which terminates the polymerization. This extension reaction is preferably carried out in separate reaction mixtures in the presence of the oligonucleotide primer that is specifically labelled by the labelling reaction, the polymerase, the nucleic acid to be sequenced as a template, the four unlabelled deoxyribonucleoside triphosphates and in each case one chain termination molecule. In this process a nucleic acid strand is formed by extension of a primer which carries a marker group which is specific for the respective primer and which is terminated by the incorporation of a chain termination molecule.

Hence the nucleic acid sequence is preferably determined by the method according to the invention by (d1) dividing the reaction mixture, after attaching the labelled deoxyribonucleoside triphosphate, into several mixtures, adding an extension reagent to each mixture which contains four unlabelled deoxyribonucleoside triphosphates and in each case a different chain termination molecule and incubating the mixtures, (d2) separating the nucleic acid fragments resulting from (d1) according to size and (d3) determining the nucleic acid sequence by means of the labelling of the individual fragments.

In the extension reaction the four unlabelled dNTPs are in a large excess compared to the labelled dNTP used in the labelling reaction so that no further incorporation of labelled dNTP takes place during the extension reaction. The unlabelled deoxyribonucleoside triphosphates are preferably in an at least 100-fold excess, preferably in an at least 1000-fold excess relative to the labelled deoxyribonucleoside triphosphates. Therefore the concentration of the unlabelled dNTPs is preferably 0.05–5 mmol/liter and particularly preferably 0.1–2.5 mmol/l liter in the extension mixture.

It is expedient to use deoxyribonucleoside triphosphates as chain termination molecules which are modified at the 3' position of the deoxyribose in such a way that they have no free OH group but are nevertheless accepted as a substrate by the polymerase. Examples of such chain termination molecules are 3' fluoro, 3'-O-alkyl and 3'H-modified deoxyribonucleosides. 3'-H-modified deoxyribonucleotides are preferably used as chain termination molecules i.e. dideoxyribonucleoside triphosphates (ddNTP). It is preferable to use unlabelled chain termination molecules in the method according to the invention but it is also possible to use labelled chain termination molecules as known to a person skilled in the art.

The determination of the nucleic acid sequence by means of the label is usually carried out by separating the labelled nucleic acid fragments according to length. This separation can be carried out according to all methods known in the state of the art e.g. by various electrophoretic (e.g. polyacrylamide gel electrophoresis) or chromatographic (e.g. HPLC) methods, a gel electrophoretic separation being preferred. Furthermore the labelled nucleic acids can be separated in any desired manner i.e. manually, semiautomatically or automatically, but the use of an automated sequencer is generally preferred. In this case the labelled nucleic acids can be separated in ultrathin plate gels of 20–500 μm preferably 100 μm thickness (see e.g. Stegemann et al., Methods in Mol. and Cell. Biol. 2 (1991), 182–184) or capillaries. However, the sequence can also be determined in non-automated devices e.g. by a blotting method.

If only a very small amount of the nucleic acid to be sequenced is available for a sequence determination according to the inventive method, an amplification step can also be carried out. One method of amplification is to carry out one or several cycles of a polymerase chain reaction (PCR) using two primers before the actual sequencing. The PCR is usually carried out without labelled dNTP. Thus the nucleic acid to be sequenced can be amplified before carrying out the actual sequencing procedure. On the other hand the amplification step can also be carried out with the aid of a thermocycling reaction. The thermocycling reaction corresponds to a normal sequencing reaction which, however, is carried out in several cycles like a PCR. The reaction mixture contains the nucleic acid template, the primer molecules, the dNTPs and the appropriate chain termination molecules as well as the polymerase which is preferably thermostable. In this manner a certain amount of the labelled nucleic acid fragments are always synthesized per cycle and large amounts of labelled fragments can be produced in several cycles.

The nucleic acid to be sequenced can be present in a single-stranded as well as in a double-stranded form. Good results are obtained when the nucleic acid to be sequenced is located on a double-stranded DNA sector e.g. a plasmid, cosmid, bacteriophage (lambda or P1), a viral vector or an artificial chromosome.

A further subject matter of the invention is a reagent kit for the selective introduction of a single labelling group into a nucleic acid which, in addition to the other components necessary for the labelling or sequencing, contains at least two labelled deoxyribonucleoside triphosphates which each contain different labelling groups and different bases. The reagents can for example be present in the form of a solution, a suspension or a lyophilisate. This reagent kit can be used in particular to sequence nucleic acids and can contain additional reagents (e.g. enzyme, primer, buffer solutions, unlabelled dNTPs, terminators).

It is intended to elucidate the invention by the following examples in conjunction with FIGS. 1–4.

EXAMPLE 1

Simultaneous DNA Sequencing Using Two Primers cDNA molecules derived from a human keratinocyte-cDNA bank were cloned according to standard methods into a Bluescript vector (Stratagene, LaJolla, Calif., USA). The plasmid DNAs were purified using Quiagen (Hilden, Germany) or Nucleobond AX ion exchanger columns (Macherey-Nagel, Duren, Germany).

All primers were developed using the computer programme gene skipper (EMBL, Heidelberg, Germany) or Oligo™, 4.1 (Medprobe, Oslo, Norway). Primer pairs were selected which do not have a tendency to form dimers and which had no further binding sites on the template or no tendency to form a hairpin structure. One of the primers was selected such that an "A" is attached as the next base to the 3' end. The second primer was selected such that a "C" is attached as the next base. The primers were synthesized on the multiple segment DNA synthesizer from EMBL (Ansorge et al, Electrophoresis 13 (1992) 616–619).

The following reaction protocol was used for the sequencing.

1. Denaturing and Annealing

5–10 μg double-stranded DNA (5–8 kb) was mixed with 2 unlabelled primer molecules (in each case 2 pmol in a total volume of 12 μl) and denatured by adding 1 μl 1 mol/1 liter NaOH solution and heating to 65° C. for 3 minutes. After cooling for one minute to 37° C. and briefly centrifuging, 1 μl 1 mol/liter HCl and 2 μl annealing buffer (1 mol/liter Tris/HCl pH 8, 0.1 mol/liter $MgCl_2$) were added.

2. Labelling Reaction

In each case 1 μl 10 μmol/liter fluorescein-15-dATP, 10 μmol/liter Texas red-5-dCTP and either native T7 DNA polymerase (8 U/μl) or Sequenase (13 U/μl) were added to the above mixture. The reaction mixture was incubated for 10 min. at 37° C.

3. Extension and Termination

1 μl extension buffer (304 mmol/liter sodium citrate, 40 mmol/liter $MnCl_2$, 324 mmol/liter dithiothreitol) was added to the mixture and mixed. Then the solution was divided into aliquots and added to 4 separate extension/termination mixtures which were composed of 3 μl of the respective termination solutions (40 mmol/liter Tris/HCl pH 7.4, 50 mmol/liter NaCl, 5 μmol/liter of the respective ddNTP, 1 mmol/liter each of DATP, dCTP, $C^7$-dGTP and dTTP) and 1 μl DMSO. The reaction was incubated for 5 min at 37° C. and terminated by addition of 4 μl stop solution (6 mg/ml dextran blue and 20 mmol/liter EDTA, pH 7.3 in deionised formamide). Then the samples were denatured for 4 min at 85° C. and applied to a sequencing gel.

4. DNA Sequencer

The structure of the modified DNA sequencer is described in detail by Wiemann et al (Anal. Biochem. 224 (1995), 117–121). In addition to the usual argon laser detector system, a helium neon laser with a corresponding detector was also mounted in the sequencing device. The Ar laser excites the fluorescein-labelled samples whereas the HeNe laser is used to excite Texas red-labelled DNA fragments. Both laser rays are passed into the gel with the aid of a single light coupling plate which is arranged between two spacers on one side of the gel. The spatial distance of 0.7 cm between the lasers and the combination of two different lasers, detector and filter systems with corresponding fluorophores ensures that there is no cross-detection of the sequence signals.

5. Gel Electrophoresis

The DNA fragments were separated on denaturing 6.5% Duracyl (Millipore, Bedford, Massachusetts, USA) sequencing gels. The separation was carried out over a distance of 18.5 cm in the case of the Texas red-labelled fragments and of 19.2 cm in the case of the fluorescein-labelled fragments using standard A.L.F. (Pharmacia, Uppsala, Sweden) glass plates. The sequences of both reactions were detected on-line and stored in a computer.

Figure 1:
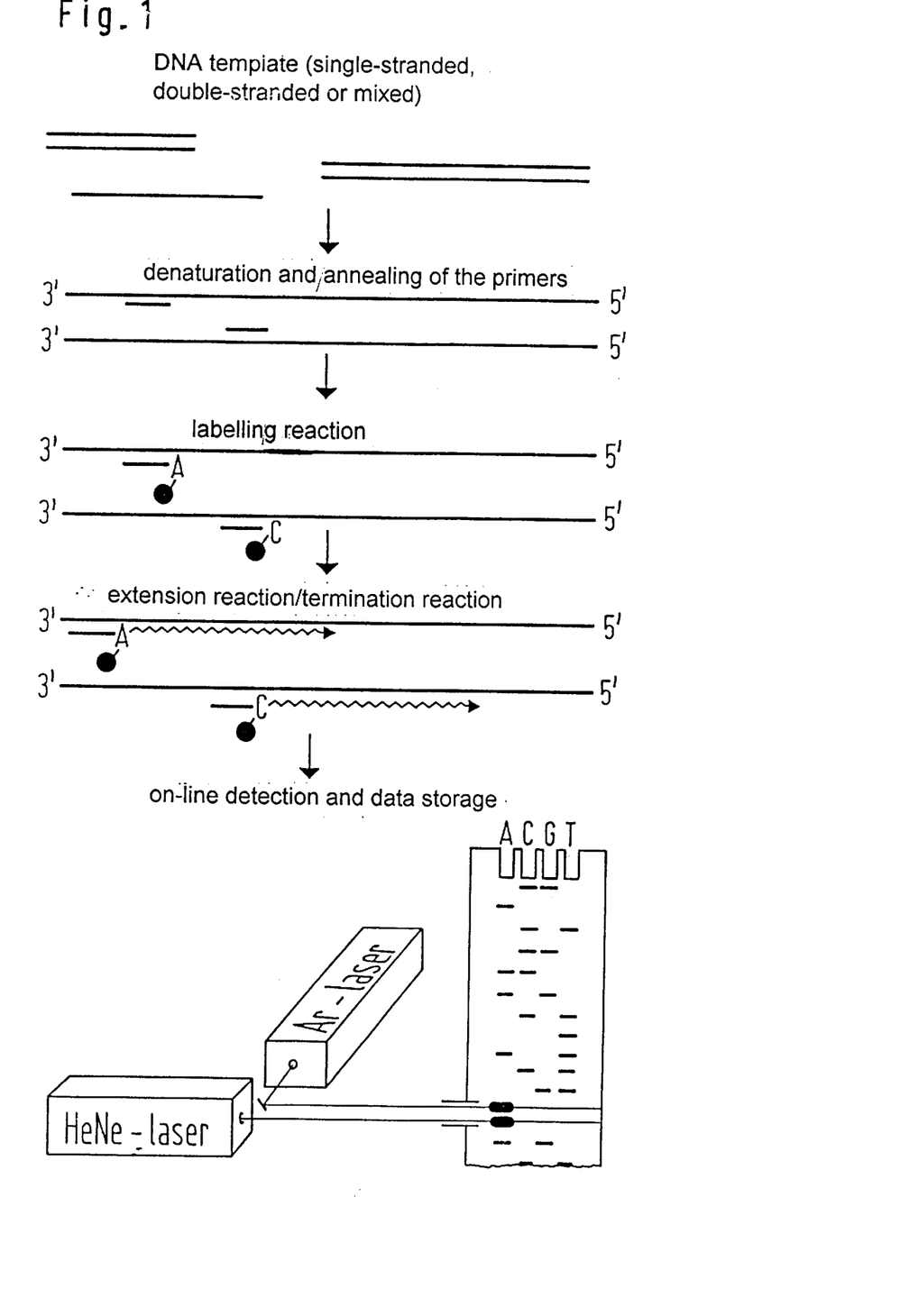
FIG. 1 shows a diagram of the sequencing procedure according to the invention.

FIG. 1 shows a diagram of the principle of the simultaneous sequencing of nucleic acids. After denaturation two primers bind to their respective complementary regions on the nucleic acid template to be sequenced. The templates can be derived from the same strand of a single-stranded or double-stranded DNA or from different strands of the same double-stranded DNA or from different DNAs. Two differently labelled dNTPs are used in the sequencing reaction. In the labelling step of the sequencing reaction only the two labelled nucleotides fluorescein-15-dATP and Texas red-5-dCTP are present.

A selective labelling of specific products with only one dye is achieved by incorporating the respective nucleotide as the first base directly downstream of the primer molecule. This reaction is comparable to the minisequencing (Syvänen et al, Genomics 8 (1990), 684–692) of point mutations in which bases attached directly to the primer are the factor which distinguishes whether a labelled dNTP is incorporated or not incorporated. The primers are selected such that the bases which are attached directly to the primers are different e.g. an "A" and a "C". In this labelling step only the correct nucleotide is always incorporated into each primer. After incorporation of the first labelled dNTP the polymerase can have a break since the labelled dNTPs are present only at a low concentration. The polymerase could also fall from the template and be available to extend further primer molecules up to the incorporation of the labelled dNTPs (e.g. in cycle sequencing).

No further labelled dNTP is incorporated in the extension and termination reaction due to a large excess of unlabelled dNTP.

Figure 2A:
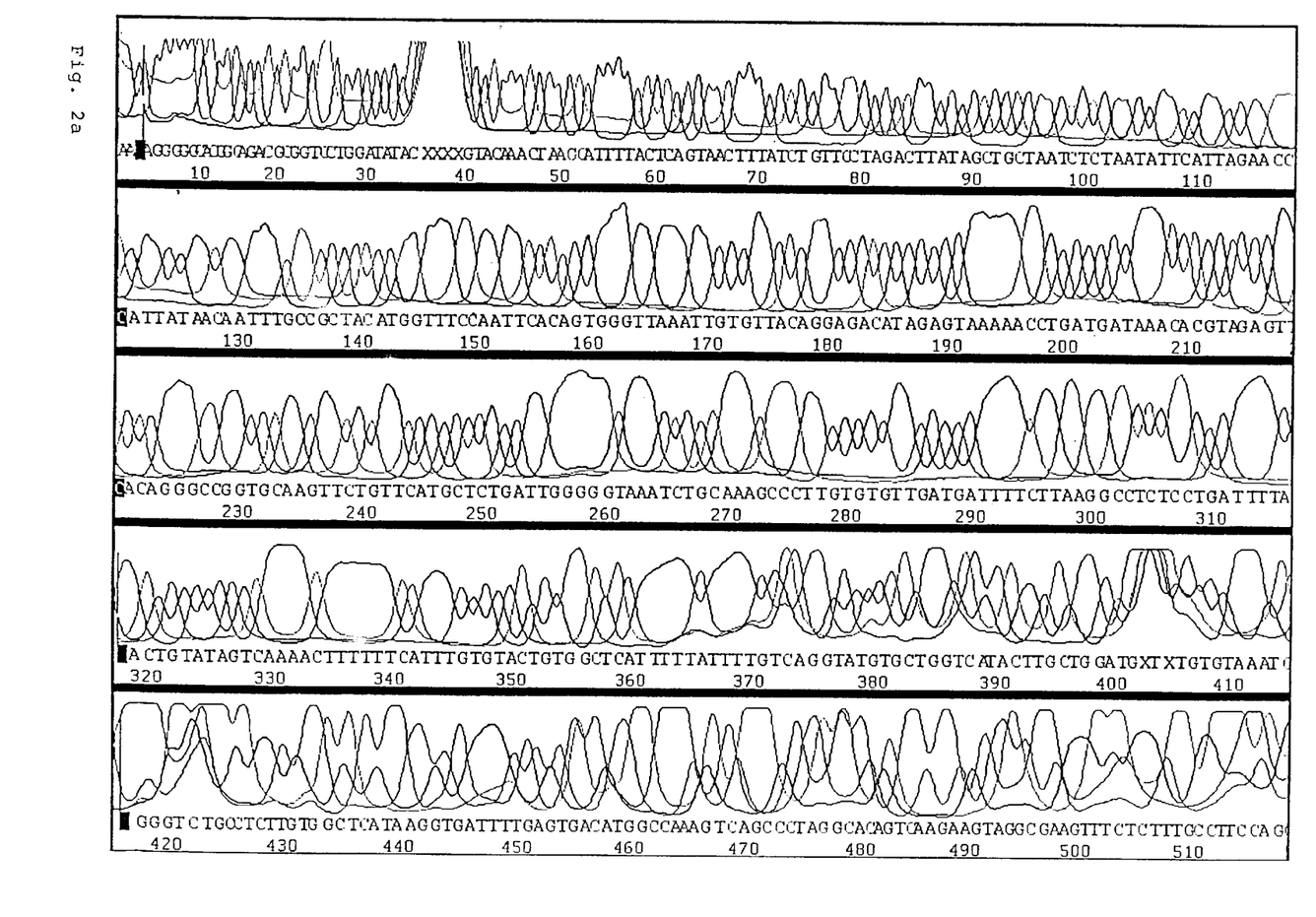
FIG. 2a and FIG. 2b shows the result of a plasmid sequencing with simultaneous use of two unlabelled primers in the presence of fluorescein-15-dATP and Texas red-5-dCTP.
Figure 2B:
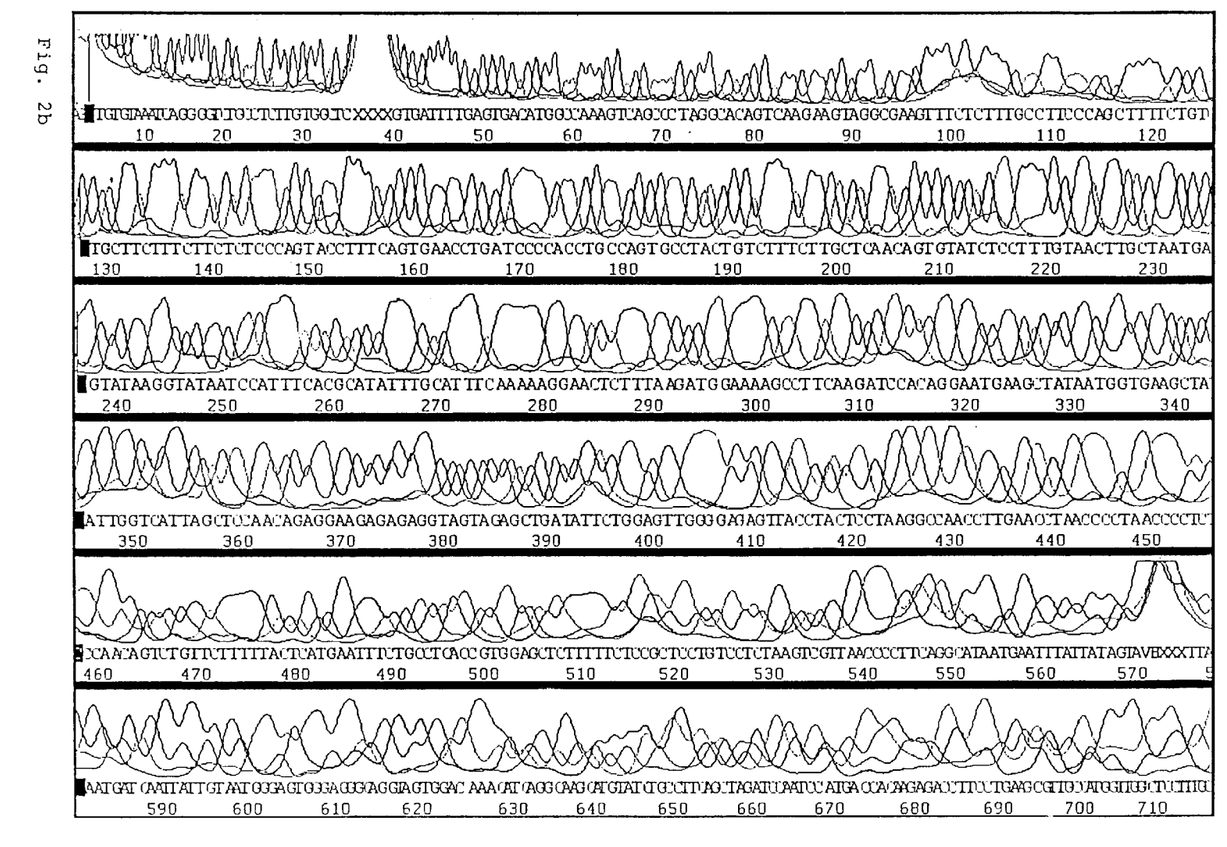

FIG. 2 shows sequence data that were obtained in a simultaneous sequencing on both strands of a plasmid DNA. Two unlabelled walking primers were used. FIG. 2a shows the sequence generated with fluorescein-15-dATP and FIG. 2b shows the sequence generated with Texas red-5-dCTP.

Figure 3:
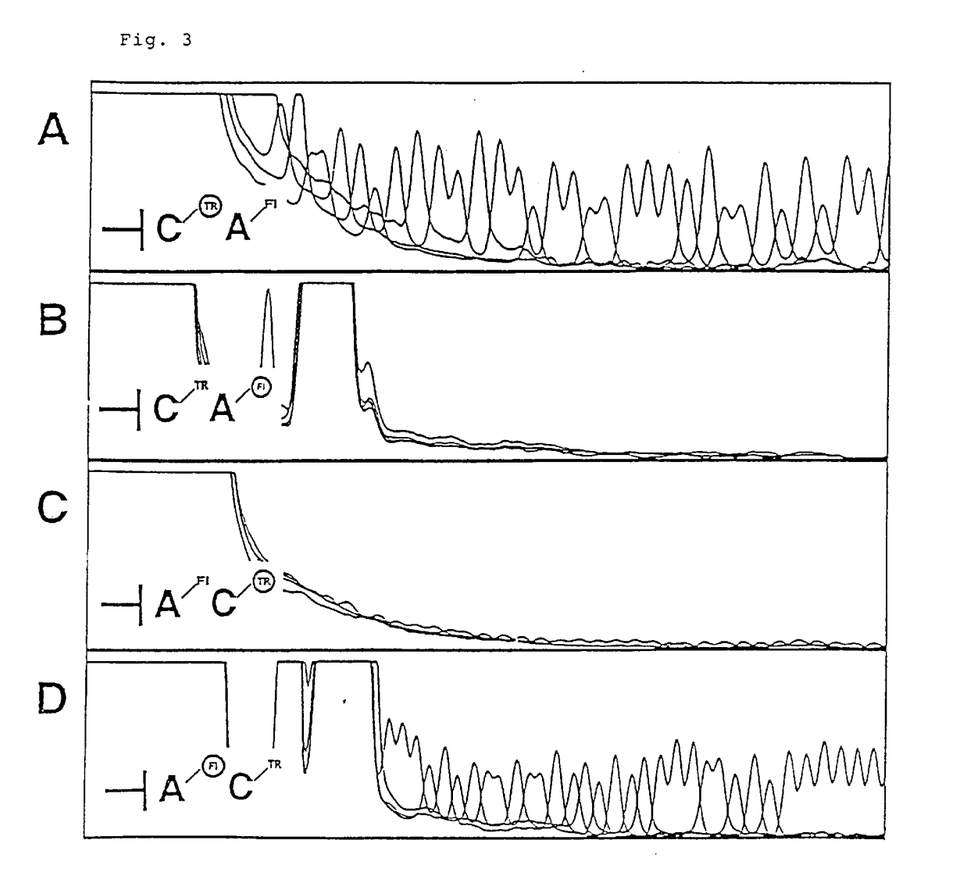
FIG. 3 shows the result of an investigation of the severalfold incorporation of labelled dNTP and FIG. 4 shows the result of an investigation regarding the incorporation of a label into the primer itself.

FIG. 3 shows the result of a test for multiple incorporation of labelled dNTP. Sequencing primers were selected with which firstly a "C" and then an "A" or firstly an "A" and then a "C" are incorporated at positions +1 and +2. The sequencing reactions were carried out with native T7 DNA polymerase. FIG. 3a shows the Texas red signals of a primer with a "C" at position +1 and an "A" at position +2. FIG. 3b shows the fluorescein signals of the same primer. FIG. 3c shows Texas red signals of a primer with "A" at position +1 and a "C" at position +2. FIG. 3d shows fluorescein signals with the primer from FIG. 3c.

It can be seen in FIG. 3 that there was no incorporation of fluorescein-15-dATP at position +2 (FIG. 3b). In contrast FIG. 3c shows that there was a slight incorporation of Texas red-5-dCTP at position +2. Since labelling at pos. +2 is considerably weaker than the labelling at pos. +1, the sequence data obtained with the second primer are, however, also unequivocal.

Figure 4:
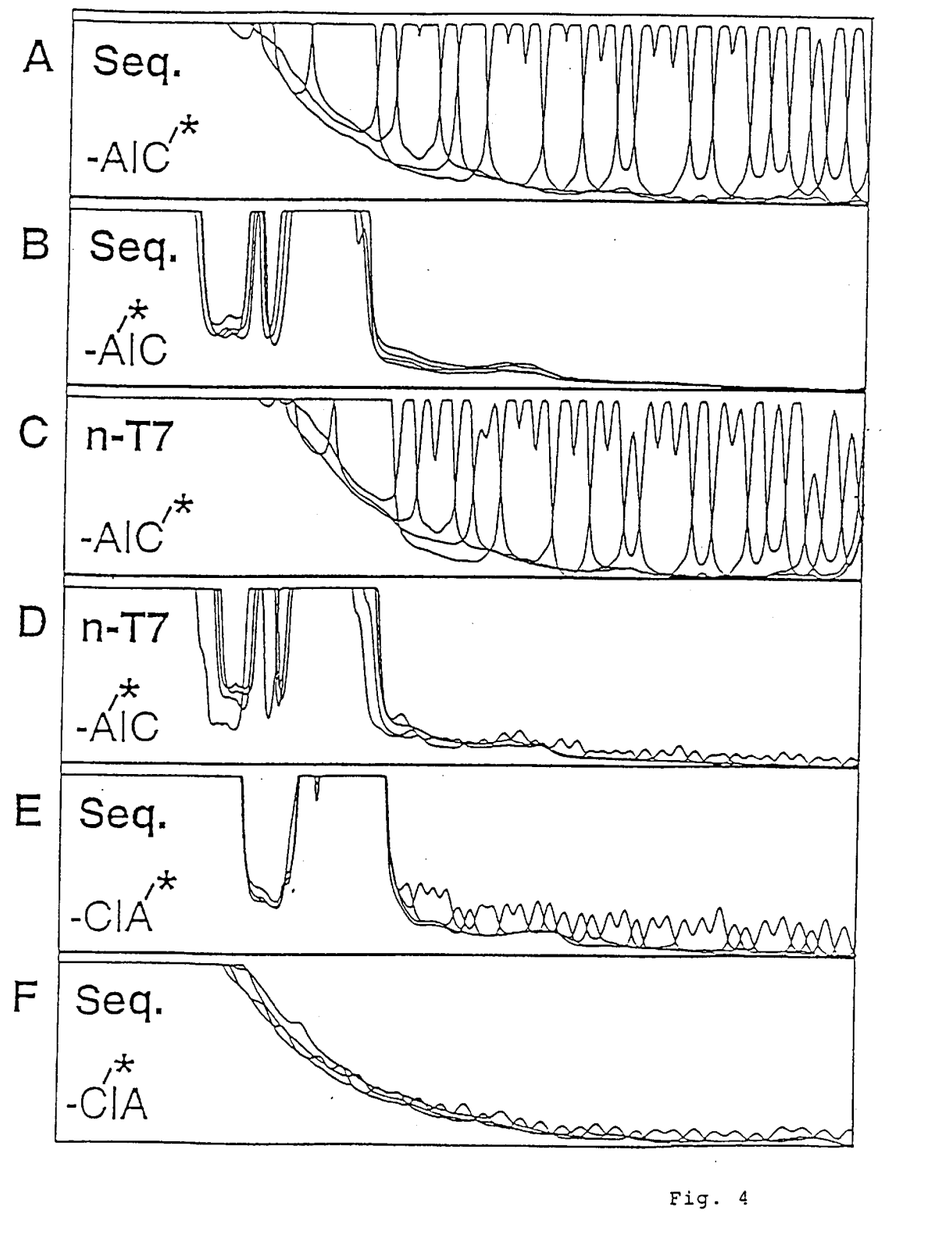

FIG. 4 shows the results of a test for the incorporation of a label within the primer. Sequencing primers are selected which contain an "A" as the 3' terminal base (position −1) and which are intended to incorporate a "C" as the next base (position +1) as well as primers with the reverse base sequence. The sequencing reactions were either carried out with native T7 DNA polymerase (n-T7) or Sequenase (Seq). FIG. 4a shows Texas red signals from a sequencing with Sequenase and a primer with "A" as the 3' terminal base and a "C" at position +1. FIG. 4b shows fluorescein signals from a sequencing with Sequenase and with the primer from FIG. 4a. FIG. 4c shows Texas red signals from a sequencing with native T7 polymerase and the primer of FIG. 4a. FIG. 4d shows fluorescein signals from a sequencing with native T7 DNA polymerase and the primer of FIG. 4a. FIG. 4e shows fluorescein signals of a sequencing with Sequenase and a primer with a "C" as the 3' terminal base and an "A" at position +1. FIG. 4f shows Texas red signals from a sequencing with Sequenase and the primer from FIG. 4e.

When the reaction was carried out with Sequenase (version 2.0) and the primer with a 3' terminal "A", only Texas red dCTP was incorporated at position +1 (FIG. 4a) whereas fluorescein dATP at position −1 was not incorporated into the primer (FIG. 4b). In contrast using native T7 DNA polymerase a slight incorporation of fluorescein-dATP was seen within the primer (position −1) (FIG. 4d).

With a "C" as the last base of the primer and an "A" as the subsequent base it was found that Texas red dCTP was incorporated at position −1 even when using Sequenase (FIG. 4f). However, due to the low signal strength there was no significant interference of the sequencing reaction.

We claim:

1. A method for the simultaneous and specific labeling of nucleic acids comprising:
   a) providing an enzymatic labelling reaction in a single reaction vessel, said reaction vessel comprising:
      i) one or more target nucleic acid molecules;
      ii) at least one nucleic acid primer molecule of a distinct sequence, wherein each primer molecule hybridizes to a distinct area of the target molecule or molecules; and
      iii) a first labelled 3' unblocked deoxyribonucleotide triphosphate of a particular base, and a second labelled 3' unblocked deoxyribonucleotide triphosphate of a different base, wherein the first labelled deoxyribonucleotide triphosphate contains a different label than the second deoxyribonucleotide triphosphate;
   b) hybridizing at least one primer molecule to the target molecule or molecules;
   c) attaching at least one of the labeled deoxyribonucleoside triphosphates to at least one primer molecule; and
   d) detecting the labeled deoxyribonucleotide triphosphates that are now attached to at least one primer molecule.

2. The method of claim 1 comprising:
   a) providing an enzymatic labelling reaction in a single reaction vessel, said reaction vessel comprising:
      i) one or more target nucleic acid molecules;
      ii) a first nucleic acid primer molecule of a distinct sequence, and a second nucleic acid primer molecule of a second distinct sequence, wherein the first primer molecule and the second primer molecule hybridize to different and distinct areas of the target molecule or molecules; and
      iii) a first labelled 3' unblocked deoxyribonucleotide triphosphate of a particular base, and a second labelled 3' unblocked deoxyribonucleotide triphosphate of a different base, wherein the first labelled deoxyribonucleotide triphosphate contains a different label than the second deoxyribonucleotide triphosphate;

b) hybridizing the first and second primer molecules to the target molecule or molecules;

c) attaching the labeled deoxyribonucleoside triphosphates to the first and second primer molecules, under conditions in which the first labelled deoxyribonucleoside triphosphate is attached to the first primer molecule, and the second labeled deoxyribonucleoside triphosphate is attached to the second primer molecule; and d) detecting the labeled deoxyribonucleotide triphosphates that are now attached to the first and second primer molecules.

3. The method of claim 1 wherein the labeled 3' unblocked deoxyribonucleoside triphosphate is attached directly to the 3' end of each primer molecule at position +1.

4. The method of claim 1 wherein a DNA polymerase without 3' exonuclease activity is used to attach the labeled 3' unblocked deoxyribonucleotide triphosphates to the primer molecules.

5. The method of claim 4 wherein a modified T7 DNA polymerase is used.

6. The method of claim 1 wherein a DNA polymerase with 3' exonuclease activity is used to attach the labeled 3' unblocked deoxyribonucleoside triphosphates to the primer molecules.

7. The method of claim 1 wherein the labeled 3' unblocked deoxyribonucleoside triphosphate is in inserted in a substitution reaction as the last base of the primer molecule at position −1, by sequential exonuclease and polymerase activities of the DNA polymerase.

8. The method of claim 1 wherein the primer molecules do not contain labeling groups.

9. The method of claim 1 wherein the primer molecules do contain labeling groups, and the labeling groups on the primer molecules are not the same as the labeling groups on the first or second labeled 3' unblocked deoxyribonucleoside triphosphates.

10. The method of claim 1 wherein the labeling group on the primer molecules are selected from the group consisting of fluorescent dyes, metals, biotin and digoxigenin.

11. The method of claim 1 wherein the labeled 3' unblocked deoxyribonucleoside triphosphates are used at a concentration of 0.05 to 5 μmol/liter.

12. The method of claim 11 wherein the labeled 3' unblocked deoxyribonucleotide triphosphates are used at a concentration of 0.1 to 2.5 μmol/liter.

13. The method of claim 1 wherein two different Drimer molecules are used and wherein the primer molecules are selected in such a way that the base to be attached at the 3' end of the first primer molecule is different from the base to be attached at the 3' end of the second primer molecule.

14. The method of claim 1 wherein two different primer molecules are used and wherein the base to be attached at the 3' end of the first primer molecule at position +1 is not the same as the base that could be attached as position +2 of the second primer molecule.

15. The method of claim 1 wherein two different Drimer molecules are used and wherein the base to be attached at the 3' end of the first primer molecule at position +1 is not the same as the base that could be attached at position +1 of the second primer molecule.

16. The method of claim 1 wherein the first and the second 3' unblocked deoxyribonucleoside triphosphates contain different fluorescent labeling groups.

17. The method of claim 16 wherein the fluorescent labeling groups are selected from the group consisting of fluorescein or derivatives thereof, Texas red, rhodamine or derivatives thereof, phycoerythrin, CY3, CY5, CY2, CY7, coumarin, infrared 40, MR 200, bodipy dyes, IRD 40 and 1,$N^6$-ethano modification groups.

18. The method of claim 16 wherein the different fluorescent labeling groups can be detected simultaneously.

19. The method of claim 16 wherein two or more different lasers are used for detection.

20. The method of claim 16 wherein a laser is used for detection.

21. A method for the simultaneous sequencing of nucleic acids comprising:

a) providing an enzymatic labelling reaction in a single reaction vessel, said reaction vessel comprising:

i) one or more target nucleotide molecules;

ii) a first nucleic acid primer molecule of a distinct sequence, and a second nucleic acid primer molecule of a second distinct sequence, wherein the first primer molecule and the second primer molecule hybridize to different and distinct areas of the target molecule or molecules; and iii) a first labelled deoxyribonucleotide triphosphate of a particular base, and a second labelled deoxyribonucleotide triphosphate of a different base, wherein the first labelled deoxyribonucleotide triphosphate contains a different label than the second deoxyribonucleotide triphosphate;

b) hybridizing the first and second primer molecules to the target molecule or molecules;

c) attaching the labeled deoxyribonucleoside triphosphates to the first and second primer molecules, under conditions in which the first labelled deoxyribonucleoside triphosphate is attached to the first primer molecule, and the second labeled deoxyribonucleoside triphosphate is attached to the second primer molecule;

d) dividing the reaction mixture from the single vessel into separate vessels, and adding an extension reagent, wherein each vessel contains four unlabeled deoxyribonucleoside triphosphates and, in each separate vessel, a different chain termination molecule, e) separating the nucleic acid fragments formed in d); and f) detecting the labels on the first and second deoxyribonucleotide triphosphates and determining the sequence of the target molecules.

22. The method of claim 21 wherein the deoxyribonucleoside triphosphates are used at a concentration of 0.05–5 mmol/liter.

23. The method of claim 22 wherein the deoxyribonucleoside triphosphates are used at a concentration of 0.1–2.5 mmol/liter.

* * * * *